United States Patent [19]
Weaver

[11] Patent Number: 4,916,060
[45] Date of Patent: Apr. 10, 1990

[54] PROCESS FOR CHEMICAL MEASUREMENT IN SMALL VOLUME SAMPLES BY FLUORESCENT INDICATORS

[75] Inventor: James C. Weaver, Sudbury, Mass.

[73] Assignee: Massachusetts Institute of Technology, Cambridge, Mass.

[21] Appl. No.: 372,127

[22] Filed: Jun. 27, 1989

Related U.S. Application Data

[63] Continuation of Ser. No. 776,936, Sep. 17, 1985, abandoned.

[51] Int. Cl.$^4$ .............................................. C12Q 1/02
[52] U.S. Cl. .......................................... 435/29; 435/4; 435/7; 436/94; 436/800
[58] Field of Search ................. 435/4, 7, 29; 436/800, 436/94

[56] References Cited

U.S. PATENT DOCUMENTS

| | | | |
|---|---|---|---|
| 3,560,754 | 2/1971 | Kamentsky . | |
| 3,710,933 | 6/1973 | Fulwyler . | |
| 3,790,492 | 2/1974 | Fulwyler . | |
| 4,146,604 | 3/1979 | Kleinerman | 436/800 |
| 4,162,282 | 7/1979 | Fulwyler . | |
| 4,397,944 | 8/1983 | Komura et al. | 436/163 |
| 4,399,219 | 8/1983 | Weaver | 435/34 |
| 4,401,755 | 8/1983 | Weaver | 435/34 |
| 4,520,110 | 5/1985 | Stryer et al. | 436/800 |
| 4,542,104 | 9/1985 | Stryer et al. | 436/800 |
| 4,582,791 | 4/1986 | Khanna et al. | 436/800 |
| 4,677,060 | 6/1987 | Valet et al. | 436/163 |

OTHER PUBLICATIONS

Murphy et al.–J. of Cell Biology, vol. 98 (1984) pp. 1757-1762.
Weaver et al., *Ann. N.Y. Acad. Sci.*, 434:363-372 (1984).
Kirkbright, *Indicators*, R. Belcher and H. Frieser (Eds.), Pergamon Press, Oxford, 685-708 (1972).
Haughland, *Handbook of Fluorescent Proes and Research Chemicals*, Molecular Probes, Junction City, 1985.

*Primary Examiner*—Sam Rosen
*Attorney, Agent, or Firm*—Hamilton, Brook, Smith & Reynolds

[57] ABSTRACT

Detection or measurement of chemical indicator paramaters such as pH or of the concentration reactants of chemical reactions is accomplished by employing at least two fluorescent species with predominant emission at different optical wavelength regions, such that a synthesized fluorescence color change is created. In this manner, measurement is improved and simple visual inspection can reveal whether or not a chemical reaction or parameter has changed significantly, while retaining the sensitivity of fluorescence measurement or detection.

21 Claims, No Drawings

PROCESS FOR CHEMICAL MEASUREMENT IN SMALL VOLUME SAMPLES BY FLUORESCENT INDICATORS

The Government has rights in this invention pursuant to Grant Number NIH-5-R01GM34077-02 awarded by the National Institutes of Health.

This is a continuation of application Ser. No. 776,936 filed on Sept. 17, 1985, now abandoned.

BACKGROUND OF THE INVENTION

This invention relates to a process for determining the presence and/or concentration of a material in a small sample by utilizing at least two fluorescent indicators in the sample and detecting fluorescent color changes of at least one indicator in the sample.

Detection or measurement of chemical parameters such as pH and of chemical reactant concentrations by optical methods is well established. Such methods are generally valuable in chemistry, biology, medicine and related fields, for purposes of detection, measurement and related diagnostic tests. Optical measurement or detection is recognized as particularly valuable because optical methods are generally non-contacting, often nonperturbing, reasonably specific and very rapid. More specifically, optical methods such as colorimetry or light absorbance are particularly valuable for use with diagnostic tests in medicine and other fields, because a quantitative measurement or a simple, rapid, visual inspection allows determination or detection of a diagnostic result.

The process of colorimetric optical measurement consists of measuring the absorption of light by a sample at different wavelengths. Colorimetric optical indicators have the desirable property of being easily measured, or of exhibiting a readily distinguishable color change by simple visual inspection. Typically, a sample is illuminated by optical radiation containing a wide range of wavelengths, such that relatively different amounts of absorption are revealed as a readily perceived color. A general property of colorimetric detection or measurement is that the intensity of light transmitted by a sample is governed approximately by Beer's Law, which is given below.

$$I(\lambda) = I_o C^{\epsilon(\lambda)Cd}$$

where $I(\lambda)$ is the transmitted light intensity, $I_o(\lambda)$ is the incident light intensity, $\epsilon(\lambda)$ is the molar extinction coefficient, C is the concentration of the optical indicator or dye, d is the optical path length and $\lambda$ is the light wavelength. An important consequence is that colorimetric detection or measurement of small amounts or concentrations of chemical indicators, or of chemical reactant, is essentially obtained from the difference or ratio of two large parameters, the first parameter being the incident optical intensity and the second parameter being the transmitted optical intensity. It is well known that detection or measurement based on a small difference, or on ratios, between two large parameters is generally inaccurate, because the magnitude of the noise or error in each of the two large parameters tends to be large compared to the difference or ratio in the two large parameters. In essence colorimetric measurement involves measurement in the presence of a large background intensity, whereas fluorescence measurement does not. For these reasons, a significant disadvantage of colorimetric optical measurement or detection is that the sensitivity or detection limit for the underlying chemical indicator or reactant concentration is much poorer than for fluorescence measurement.

A further, related disadvantage applies to colorimetric detection or measurement carried out on very small size samples. This is important, because it is becoming generally desirable to carry out chemical detection and measurement using small samples, particularly in biological and medical tests. As indicated by Beer's Law, the logarithm of the ratio, y $[I(\lambda)/I_o(\lambda)]$, of transmitted to incident optical intensity is proportional to the product of three quantities: (1) $\epsilon(\lambda)$, the molar extinction coefficient, which is a property of a particular chemical indicator species or of a particular chemical reactant, (2) C, the concentration of the indicator or reactant, and (3) d, the optical path length within the sample. In the important case of small samples, most particularly samples with a maximum linear dimension of about 1000 micron ($10^{-1}$ cm) down to about 1 micron ($10^{-4}$ cm), the indicator or reactant concentration must be significantly larger than is the case for conventional measurement using conventional optical cuvetts with a standard optical path length of 1.0 cm. The desirability of detection and measurement in small samples such as liquid or gel microdroplets is increasingly recognized as disclosed, for example, in U.S. Pat. Nos. 4,399,219 and 4,401,755 and in Enzyme Engineering 7, Vol. 434, reprinted from Annals of the New York Academy of Sciences, pp. 363-372, Weaver et al. Small samples which are approximately spherical in shape have maximum optical path lengths equal to the spherical diameter, so that for the case of optical path lengths in the range $10^{-1}$ to $10^{-4}$ cm, the corresponding sample volumes are very small, in the range $5.2 \times 10^{-4}$ ml to $5.2 \times 10^{-13}$ ml. More specifically, for small samples with optical path lengths in this range of $10^{-1}$ to $10^{-4}$ cm, in order to obtain the same perceived color, or to make a measurement with essentially the same optical accuracy, the indicator or reactant concentration must be present at a concentration which is a factor about $10^1$ to $10^4$ larger than in the conventional arrangement using a 1 cm path length. This results in the undesirable degradations of the detection or measurement ability by the same factor of about $10^1$ to $10^4$ for colorimetric detection or measurement in small samples.

An important related problem arises when chemical indicator species are employed to detect or measure parameters such as pH. The requirement of a large concentration of indicator species because of the small optical path length often results in a degradation of detection or measurement performance because of an interaction of the highly concentrated indicator with a primary chemical reaction within the small volume. For example, in the important case of detection or measurement of acid production from a single or small number of micororganisms or other biochemically active entity within a small volume sample, the presence of a high concentration of pH indicator species can significantly increase the buffering capacity within the small sample, and thereby significantly reduce the ability to rapidly detect or measure acid production with the small volume sample.

In the important case of direct, visual inspection, colorimetric measurement based on color change has the desirable property of allowing simple, rapid assessment of whether or not a chemical change has occured. For example, in the well-known and important case of acid-base determination wherein pH is used as an indicator, there are a variety of well-known colorimetric pH indicators which are known to give useful perceived color changes over a useful range of pH values. Examples of colorimetric pH indicators and typical corresponding ranges of useful pH are methyl violet (pH 0.1–1.5), bromphenol blue (pH 3.0–4.6), methyl red (pH 4.8–6.0), bromothymol blue (pH 6.0–7.6), phenolphthalein (pH 8.2–10) and 1,3,5-trinitobenzene (pH 11.5–15.0). In contrast, visual inspection as the basis of the change in absolute intensity of transmitted light at one relatively narrow band of wavelengths is significantly more difficult, because it is more difficult to visually determine changes in optical intensity than to determine changes in color.

Fluorescence measurement is often based on changes in intensity of the emitted light for fixed excitation light conditions. Relatively few fluorescent indicators exhibit a large change in the relative strength of emission as a function of wavelength as a chemical parameter such as pH varies. Instead, fluorescence measurements are generally carried out on the basis of changes of total intensity, using only a single fluorescent species as a chemical indicator or a chemical reactant. In contrast to the availability of colorimetric indicators, fluorescent species which respond to changes in an exemplary chemical parameter such as pH generally usually exhibit only a large variation in strength of total fluorescence emission, which property, therefore, does not allow a determination to be made on the basis of a perceived color change.

For example, Kirkbright, "Fluorescent Indicators" in *Indicators*, R. Belcher and H. Frieser (Eds.), Pergamo Press, Oxford, pp. 685–708, (1972), lists seventy six (76) fluorescent indicators for pH, of which only twenty-four (24) actually change emission color, while the remaining thirty-two (32) only change emission intensity at the same color. Further, of these twenty-four (24), only eight (8) are potentially useful in the broad physiological pH range of about 5<pH<9, and only four (4) are potentially useful in the more important physiological range 6<pH<8. Finally, the pH range over which the color change of a single fluorescent indicator species is significant is generally broad, making visual observation difficult (Kirkbright, 1972), and the pH at which the maximum change occurs may not correspond to a desirable pH, and cannot be significantly altered. Several other fluorescent pH indicators, which generally have these properties are described by Haugland, *Handbook of Fluorescent Probes and Research Chemicals*, Molecular Probes, Junction City, (1985).

For example, in the case of intracellular pH measurements using fluorescence, wherein the cell volume comprises a small volume sample, it has been found to be generally necessary to use complex instrumentation to exploit relatively small change in the relative emission in different wavelength bands of the emission spectrum of a single dye which is taken up or contained within a living cell. However, the small changes exploited in these intracellular pH measurements are generally too small to be used as the basis of a readily perceived color change. Instead, a relatively complex measurement procedure must be used. In partial summary, the advantage of a readily perceived color change is generally not obtained from the established use of fluorescence indicators or fluorescent products of chemical reactions.

The overall teaching of the prior art is that in the case of measurement of reactant concentrations by fluorescence means in small volume samples, a single fluorescent species is used if a reactant is measured or determined. Similarly, the overall teaching of the prior art is that in the case of measurement based on fluorescent chemical parameters in small volume samples, a single fluorescent species is used as an indicator.

Accordingly, it would be highly desirable to provide a simple-to-use optical indicator methodology which would have significantly better sensitivity or detection limits than conventional colorimetry for chemical parameter or chemical reactant concentration while still retaining the advantage of a color change while still providing an indicator means which can also be advantageously employed in instruments and to provide improved fluorescence means of measuring indicator or reactant concentrations in small volume samples.

SUMMARY OF THE INVENTION

In accordance with this invention, at least two fluorescent species are employed for use in small volume samples, in suitable relative concentration so as to allow the creation of a fluorescent color change due to the simultaneous presence of the emission light from several fluorescent species changes, at least one of which species serves as a chemical parameter or serves as a chemical reactant. For example, in the important case of acid-base determination wherein pH is used as a parameter, two fluorescent species can be employed, even though neither by itself exhibits significant shift in its relative strength of fluorescence emission at different wavelengths, in order to create a color change due to fluorescence. More specifically, in the case of a pH indicator, a first fluorescent species is selected which has a significant increase in total fluorescence emission intensity as pH varies over some useful range, and a second fluorescent species which is a reference standard, is selected which has a significant decrease, no change or a smaller increase, in total fluorescence emission intensity as pH is varied over the same range. Both fluorescent species are simultaneously excited by the same source of optical excitation radiation, such as a mercury arc lamp or other suitable means, so that a perceived fluorescent color change is created due to the change in relative emission of the two fluorescent species. By varying the relative concentration of the two fluorescent species, the pH at which the so-created fluorescent color change occurs can be varied over a useful range of pH values. More than two fluorescent species can be used in an extension of the same methodology, such that a plurality of pH ranges exist over which a color change occurs and more than one source of optical excitation light can be employed.

DESCRIPTION OF SPECIFIC EMBODIMENTS

In accordance with this invention, two or more fluorescent indicators are incorporated into a small volume sample comprising either liquid or gel microdroplets which may contain or not contain a microbiologically or biochemically active material and at least two indicators which change emission intensity differently in response to concentration or type of the microbiologically or biochemically active material. At least one of the fluorescent indicators contributes to a change in color either by increasing or decreasing fluorescent emission intensity in response to a physical property of or the concentration of the microbiologically or biochemically active material. The other fluorescent indicator is a reference standard, which either does not change intensity of emission in response to a change in the concentration or activity of the microbiologically or biochemically active material or does change intensity of emission to a level opposite to the change of intensity of emission of the first fluorescent indicator in response to the same change in concentration or physical property which drives the change in the first fluorescent indicator, or changes in the same direction as the first, but less sensitively.

The term "detecting" as used in the specification and claims herein means the capacity to determine the presence or absence of a material in a sample and/or determining the concentration of a material in a sample.

Microbiologically or biochemically active materials having a small size such as yeast, bacteria, mold, enzymes or the like are suspended in an aqueous medium which may or may not be capable of gelatin upon subsequent treatment of the suspending medium.

In the case of gelable media, suitable gel suspending media include water soluble natural gel material and synthetic water soluble polymers. Suitable liquid suspending mediums are aqueous mediums which do not gel and which do not adversely affect the active materials in the sample. Representative suitable materials include agarose, fibrinogen, kappa-carrageenan, iota-carrageenan, sodium alginate, furcellaran, zein, succinylated zein, succinylated cellulose or the like. Representative suitable synthetic water soluble polymers include those formed from vinyl pyrolidone, ethyl succinate cellulose 2-methyl-5-vinyl pyrridinemethyl acrylate-methacrylate acid copolymer, vinyl alcohol, vinyl pyrridine, vinyl pyrridine-styrene copolymer or the like. The microbiologically or biochemically active material is suspended in the suspending medium at a dilution which is selected using knowledge of the volume of the gel microdroplet (GMD) to be produced and an estimate of the density or size of cells or molecules in the first liquid medium.

In a preferred form of this invention, the droplets are formed so that there is a high probability that each droplet contains a desired number or less of microbiologically active material. This can be effected by regulating the dilution of the liquid composition to be produced to droplets, a knowledge of the size of the microbiologically active material and the size of the droplets to be produced. The regulation of these factors can be determined by conventional Poisson statistical analyses so that the number of droplets containing more than the desired number of microbiologically active materials is more than two standard deviations from the mean. It is desirable for example, to isolate zero to one microbiologically active cell per droplet in recombination DNA research where it is desired to isolate a particularly active genetically modified enzyme bacterium from a large population of such bacterium.

Gel material and nutrients can be incorporated in the suspending medium, in which case very little dilution may be desired. Thus, for example, when it is desired to have a high probability of zero to one microbiologically active material per droplet, it is only necessary to dilute the sample by more than about a factor of about 1.1, usually up to about 10 or larger if desired if the unknown cell or enzyme concentration is believed to be large. For example, if the average volume is about $10^{-7}$ ml, corresponding to a droplet with diameter about $5 \times 10^{-3}$ cm (50 $\mu$m), if spherical, significant dilution is generally not needed until the initial cell concentration reaches about $10^{-7}$ cells-ml$^{-1}$, which is a much higher concentration than encountered for most samples. For smaller spherical droplets, for example, 10 micron diameter, significant dilution is not needed until the sample concentration reaches about $10^9$ cells-ml.$^{-1}$.

For purposes of measuring microbiologically active material, it is desirable to utilize dilutions such that the suspension can be subsequently formed into droplets each of which have a high probability of containing none of the desired microbiologically active material of interest or only a single cell or molecule of the microbiologically or biochemically active material of interest. By separating and localizing the microbiologically or biochemically active material in this manner, it is possible to measure materials of desired activity, which activity is not diluted by the presence of other biologically active material not having the desired activity. For example, it may be desirable to measure bacteria such as E. coli in accordance with the process of this invention in unknown quantity. The bacteria is suspended in an aqueous medium and then converted into droplets such that there is a high probability that each droplet contains none or only one of such bacteria. The thus-produced liquid droplets are directed into a liquid medium capable of effecting gelation of the droplets, if desired. Alternatively, the initially liquid droplets can be changed in temperature or contacted with suitable gel-inducing vapors before entering a second liquid medium. In addition, the droplets also can contain a conventional bacteria growth supporting composition which permits the bacteria to metabolize and, sometimes, to replicate within the droplets, and also contains at least two fluorescence indicator dyes, of which at least one exhibits fluorescence changes with pH.

In the case of coated droplets, the first suspending medium is provided with specific nutrients or specific substrates or the like, in addition to any indicator dyes or pH shifts, in order to allow measurement of specific cells or enzymes.

This invention is useful for studying a wide variety of materials having microbiological or biochemical activity, interaction or suppression including parasites, virus, yeast, cells, bacteria mold, enzymes, interactions between variant cells, cell-virus interactions, hybridomas or the like.

Representative bacteria which can be processed in accordance with this invention include E. coli, Proteus mirablis, Pseudomonas, Staphyloccous aureus, Citrobacter freundii, Klebsiella, Lactobacillus and Saccaromyces cerevisliae.

Representative dyes which increase fluorescent emission intensity with an increase in pH include fluorescein, $\beta$-Naphthoquinoline, O-phenylenediamine or Quinoline. Representative dyes which decrease color or fluorescent emission intensity with increased pH include Luminol, 1,4-Dihydroxybenzene disulphonic acid, umbelliferone or coumaric acid. Representative dyes which do not change fluorescent emission intensity significantly over a relatively wide pH range include sulforhodamine 101, Lucifer yellow or 8-aminonaphthalene-1,3,6-trisulfonic acid. Thus, by combining (a) a dye which increases fluorescent intensity with increased pH with (b) a reference standard dye which decreases fluorescent intensity with increased pH or which does not change fluorescent intensity with increased pH, it is possible to measure a change in pH by noting the change in the difference in fluorescent emission intensity change between dyes (a) and (b) over time. This permits obtaining accurate measurements even with the small sized droplets of this invention.

Other chemical changes in droplets containing microbiologically active materials which can be measured in accordance with this invention include reduction/oxidation levels, accumulation of fluorescent products or consumption of fluorescent products. Such changes can be caused either by direct microbiological activity or by extracellular chemical assays, such as enzymatic assays, within the droplets. It is also possible to measure the concentration of a microbiologically or biochemically active reactant by measuring the change in fluorescent emission intensity and comparing the measured change with a standard curve that provides a measure of reactant concentration as a function of fluorescent emission intensity for a given incubation time period.

In the case of molecular size biologically active molecules such as enzymes, NADA or other fluorescent products or cofactors can be measured; the following procedure can be utilized in accordance with this invention. A sample containing an unknown quantity of a particular enzyme is suspended, with modest or large dilution, in a first liquid medium which contains buffering compounds (if desired), substrates, cofactors, a gelling agent and at least two fluorescent dyes. When the approximate upper limit of the concentration of cells or enzymes to be measured can be estimated, a droplet volume is selected so that there is a high probability the droplet will contain either none or one cell or enzyme molecule. If a linked enzyme assay is used, the appropriate assay is used; the appropriate additional enzymes, substrates and cofactors are also included at a relatively high concnetration. Similarly, if an assay is to be based on cell-cell interactions, one type of cell is also provided at relatively high concentration. The resulting diluted sample is then passed through a vibrating orifice or nozzle to cause formation of liquid droplets. Alternatively, the diluted sample is dispersed into a suitable liquid hydrocarbon, such as mineral oil. As described previously, the liquid droplets are caused to enter the gel state by cooling, contacting with a suitable vapor, or entering a second liquid medium. The resulting GMDs are coated with a thin layer impermeable or having controlled permeability, to the substrates, products and cofactors of the enzyme catalyzed reaction, such as phosphatidyl ethanolamine or phosphatidyl choline or the like. The coated GMDs are maintained at a suitable temperature such that the enzyme reactions are carried out, not necessarily to completion, and fluorescent product is accumulated and retained in GMDs containing a cell or an enzyme molecule. Alternatively, a fluorescent substrate can be utilized, in which case the fluorescent substrate decreases or disappears in GMDs containing a cell or an enzyme molecule.

In one embodiment, after the biologically active material within the gel microdroplets has been treated in order to effect the desired change in the material, such as by incubation or mutation, the suspension of the gel microdroplets then is processed in an apparatus having the capability of sensing change in fluorescent emission intensity of individual gel microdroplets to determine the presence or absence of a desired physical characteristic and thereafter isolating the gel microdroplets having the desired physical characteristic. For example, a portion of the liquid stream can be diverted into a secondary stream for subsequent recovery of the gel microdroplets such as is disclosed by Kamentsky, U.S. Pat. No. 3,560,754. Alternatively, the mainstream can be converted into discrete droplets by being passed through a nozzle which is vibrated such as by a piezoelectric crystal by the means disclosed, for example, by Fulwyler, U.S. Pat. Nos. 3,710,933, 3,790,492 and 4,162,282. The drops containing the gel microdroplets having the desired characteristics then can be electrically charged selectively and then passed between a pair of deflecting plates in order to selectively divert the electrically charged droplets so that they can be removed.

The following examples illustrate the present invention and are not intended to limit the same.

EXAMPLE I

Two fluorescent indicator species are used, which species have significantly different wavelength regions wherein their maximum fluorescence emission occurs, and both species can be simultaneously excited by the same band of excitation optical radiation, even though not necessarily with optimal efficiency, such that one species displays a significant increase in its fluorescence emission while the other species is a reference standard which displays a significant decrease in its fluorescence emission, as the pH decreases during acid production within a small volume sample of a microdroplet. By this process a fluorescence color change is created when a small sample(s) is viewed in a fluorescence microscope. The two exemplary fluorescent indicator species are:

1. Luminol (5-amino-2,3-Dihydro-1,4-Phthalazinedione), a "BLUE" fluorescent species, which has maximum relative fluorescence emission intensity in the wavelength range of about 420 nm to about 470 nm, has a strong increase in fluorescence as the pH decreases, which change is significant in the approximate range pH 7.0 to pH 5.5.

2. FITC (fluorescein isothiocyanate), a "YELLOW-GREEN" fluorescent species, which has maximum relative fluorescence emission intensity in the wavelength range of about 500 nm to about 540 nm, has a moderate decrease in fluorescence as the pH decreases, which change is significant in the approximate range pH 6.6 to pH 5.6, and allows, for example, a pH change from pH 6.6 to pH 6.2 to be detected.

By using both fluorescent species at a concentration ratio of $[Luminol]/[FITC]=20$, which compensates for differences in relative excitation intensity and in quantum efficiency for the wavelengths used, it is possible to synthesize an apparent color change as pH varies. Specific exemplary concentrations are $[Luminol]=5\times10^{-4}M$ and $[FITC]=2.5\times10^{-5}$ M. This change is particularly strong over the range pH 6.5 to pH 5.5, and is essentially independent of the overall intensity of fluorescence excitation. Further, a single excitation band ("ultraviolet" on an Olympus Fluorescence Microscope; S5-LB 175) is adequate for both Luminol and FITC. In this case, the highly fluorescent FITC is purposefully excited non-optimally, but still adequately. This use of one excitation band allows a single viewing, which simplifies and speeds up the process of examining small volume samples such as gel microdroplets (GMDs) under the fluoresccnece microscope. There is no need for a double exposure photograph, which could be needed if two different excitation bands were used. By changing the relative concentrations of two or more dyes, the pH at which the maximum rate of color change occurs can be adjusted.

GMDs can readily be made with diameters in the range, 10 to 100 microns, with corresponding volumes of $5.2 \times 10^{-10}$ to $5.2 \times 10^{-7}$ ml In the present example, medium which is weakly buffered is desirable, because a rapid detection of bacteria rather than prolonged bacterial growth is sought. In addition to the two fluorescent species, the medium contains:

| | |
|---|---|
| NaKPO$_4$ | at $5.0 \times 10^{-4}$ M |
| KCl | at 0.35% |
| NaCl | at 0.35% |
| Glucose | at $2.0 \times 10^{-2}$ M |
| Tryptone | at 0.05% |
| Yeast Extract | at 0.05% |

This medium is adjusted to an initial pH of 6.6, slightly above the region wherein the fluorescence color change is created. In this medium the doubling time at 37° C. for *E. coli* is 30 minutes; for *L. fermentum* it is 120 minutes, and for *S. faecalis* it is 45 minutes. Fluorescence microscope observation of GMDs statistically inoculated with such individual bacteria exhibit a synthesized color change from "GREEN" to "BLUE" in about 1 hour. A typical experimental protocol consisted of the following: Bacteria are grown up in the medium (minus dyes) to a density of about $10^9$ cell/ml. The cells are gently centrifuged, washed and then resuspended in the test medium containing ungelled agarose such that a density of about $1.5 \times 10^7$ cell/ml is obtained. This density corresponds to an average occupation of 40 micron GMDs of about 0.5.

This inoculated agarose-medium (initial pH=6.6) is rapidly dispersed into mineral oil and cooled, yielding a large number of GMDs. A small fraction (about $10^3$ of the GMDs) is placed in a small receptacle which is delineated with a calibrated grid (i.e., a Petroff-Hauser chamber). Typically, 10 to 100 GMDs are in a field of view when placed in the fluorescence microscope. GMDs thus-prepared are placed in a small oven at 37° C. and removed at intervals for observation. Initially, GMDs of all sizes fluoresce bright green. After approximately one hour, a fraction fluoresces bright blue (indicating a drop in pH to approximately 5.6), while others fluoresce bright green. More specifically, an appropriate fraction of GMDs in the 40 to 50μ range exhibits the bright blue fluorescence. In contrast, after approximately one hour, almost all of the larger (>70 diameter) fluoresce bright blue, and very few of the smaller (<30-μdiameter) have changed to blue but instead remain bright green. This result demonstrates the utility of using a created fluorescence color change to perform rapid microbiological determinations in small volume samples.

A summary of three types of such experiments is tabulated below:

| | E. coli (ATCC 25404) | L. fermentum (ATCC 9338) | S. faecalis (ATCC 2912) |
|---|---|---|---|
| Doubling time (t$_2$) | 0.5 hr | 2.0 | 0.75 hr |
| Detection in 40μGMDs | 1 hr | 1 hr | 1 hr |
| Number of cell divisions in detection time | 2 | <1 | ~1 |

The very rapid detection demonstrated in these experiments is based on the use of two fluorescent species to provide a created color change in the small volume of a microdroplet.

EXAMPLE II

In this example, one fluorescent species is selected to be insensitive to pH changes over the pH range of interest and the second fluorescent species is selected to exhibit a significant decrease in fluorescence emission as pH decreases because of acid production. The two exemplary species are:

1. FITC (YELLOW-GREEN), which is described in Example I, and which exhibits a significant fluorescence emission change with pH over the range pH 7.6 to 5.0.

2. Sulforhodamine 101/640 (RED), which has maximum relative fluorescence emission intensity in the wavelength range of about 610 to about 670 nm, has an insignificant change in fluorescence as the pH varies over the range pH 7.6 to 5.0, so that sulforhodamine is suitable for use as a reference species.

The species FITC is used at a concentration of $2.5 \times 10^{-5}$ M and the sulforhodamine is used at a concentration of $3.5 \times 10^{-4}$ M. Upon simultaneous excitation with the "BLUE" band on an Olympus Fluorescence Microscope; S5-LB 175, a created color changes from "YELLOW-GREEN" at about pH 5.5 to "ORANGE-RED" at about pH 3.7. These two fluorescent species can be used in small volume samples such as described in Example I, but at a lower useful pH range.

EXAMPLE III

In this example, one fluorescent species (Fluorescein) is selected to be a reactant of a chemical reaction, while a second fluorescent species Sulforhoamine 101/640 is employed as a reference standard. In an exemplary chemical reaction, the non-fluorescent substrate fluorescein diacetate (FAD) is enzymatically converted to the fluorescent product fluorescein and non-fluorescent acetate in the presence of esterases. A small volume sample, which is well buffered against pH changes, and within which it is desired to measure the esterase activity, is supplied with $5 \times 10^{-5}$ M Sulforhoamine 101/640 and $10^{-4}$ M FDA. Upon exposure to fluorescence radiation in the "BLUE" region of an Olympus Fluorescence Microscope, the small volume initially fluoresces a "YELLOW-GREEN" color. At a later time, when enzymatic catalyzed production of fluorescein has occured, such that the concentration of fluorescein has increased from essentially zero to $5 \times 10^{-6}$ M, the color shifts to "ORANGE-RED" due to the simultaneous fluorescence emission of both Sulforhoamine 101/640 and Fluorescein.

I claim:

1. A process for detecting a change in the concentration of a microbiologically or biochemically active material comprising:
   (a) providing microdroplets containing:
   (i) a source of the microbiologically for biochemically active material; and
   (ii) at least two fluorescent compounds wherein at least one first fluorescent compound is capable of contributing to a change in color by increasing in fluorescent emission intensity in response to a change in concentration of the microbiologically or biochemically active material, and at least one second fluorescent compound which is a reference standard, the proportion of which fluorescent compounds changes as the concentration of the microbiologically or biochemically active material changes, thereby producing a color change in fluorescent emissions from the fluorescent compounds;
(b) determining the color of the fluorescent emission from the fluorescent compounds;
(c) maintaining the microdroplets under conditions which allow the concentration of the microbiologically or biochemically active material to change; and
(d) detecting the change in the concentration of the microbiologically or biochemically active material by determining the change in color of the fluorescent emission from the fluorescent compounds.

2. A process of claim 1 wherein the detection comprises visual observation.

3. A process of claim 1 wherein the first fluorescent compounds are selected from the group consisting of: fluorescein, β-naphthoquinoline, Ophenylenediamine and quinoline.

4. A process of claim 1 wherein the second fluorescent compound does not change intensity of emission in response to a change in the concentration of the microbiologically or biochemically active material, changes intensity of emission to a level opposite to the change in intensity of emission of the first fluorescent composition or changes less sensitively in the same direction as the first fluorescent composition.

5. A process of claim 4 wherein the second fluorescent composition is selected from the group consisting of: luminol, 1,4-dihydroxybenzene disulfonic acid, umbelliferone, coumaric acid, sulforhodamine 101, lucifer yellow and 8-aminonaphthalene-1,3,6-trisulfonic acid.

6. A process of claim 5 wherein the first fluorescent compound is fluorescein and the second fluorescent compound is luminol.

7. A process of claim 1 wherein the source of microbiologically or biochemically active material is selected from the group consisting of: bacteria, plasmids, enzymes, yeasts, molds, animal cells and plant cells.

8. A process for selecting the microbiological activity of a microdroplet having a desired microbiological property from a plurality of microbiologically active subsamples lacking said desired property, comprising:
(a) forming a dilute suspension of said subsamples, in a liquid diluent capable of forming individual microdroplets upon subsequent treatment, said dilute suspension additionally containing at least two fluorescent compounds wherein at least one fiber fluorescent compound is selected such that the amount increases or decreases as a function of the microbiological property, and a second fluorescent compound which is a reference standard, said suspension contains one or zero microbiologically active subsamples;
(b) converting the suspension into microdroplets having a size of from about 0.2 to about 1000 micrometers;
(c) determining the color of the fluorescent emission from the fluorescent compounds contained within the microdroplets;
(d) maintaining the microdroplets under conditions which allow microdroplets having the desired microbiological property an opportunity to increase or decrease at least one fluorescent compound; and
(e) detecting the change in color of the fluorescent emission of at least one fluorescent compound with respect to at least one other composition, to thereby select microdroplets having the desired microbiological property.

9. A process of claim 8 wherein the detection comprises visual observation.

10. A process of claim 8 wherein the first fluorescent composition selected from the group consisting of fluorescein, β-naphthoquinoline, O-phenylenediamine and quinoline.

11. A process of claim 8 wherein the second fluorescent compound does not change intensity of emission in response to a change in the concentration of the microbiologically or biochemically active material, changes intensity of emission to a level opposite to the change in intensity of emission of the first fluorescent compound or changes less sensitively in the same direction as the first fluorescent compound.

12. A process of claim 11 wherein the second fluorescent compound is selected from the group consisting of: luminol, 1,4-dihydroxybenzene disulfonic acid, umbelliferone, coumaric acid, sulforhodamine 101, lucifer yellow and 8-aminonaphthalene-1,3,6-trisulfonic acid.

13. A process of claim 12 wherein the first fluorescent compound is fluorescein and the second fluorescent compound is luminol.

14. The process of claim 8 wherein the microbiologically active subsamples are selected from the group consisting of bacteria, plasmids, enzymes, yeasts, molds, animal cells and plant cells.

15. A process for detecting a microbiologically or biochemically produced material within a microdroplet, comprising:
(a) providing a microdroplet containing:
(i) a source of a microbiological or biochemical reaction;
(ii) at least one first fluorescent compound which is altered to produce or reduce a fluorescent emission when subjected to a microbiological or biochemical reaction provided by the source; and
(iii) at least one second fluorescent compound which is a reference standard, the proportion of which fluorescent compounds changes as the concentration of the microbiologically or biochemically produced material changes;
(b) determining the color of the fluorescent emission from the fluorescent compounds;
(c) maintaining the microdroplet under conditions which allow the source an opportunity to provide a microbiological or biochemical reaction; and
(d) detecting the change in color of the fluorescent emission from the fluorescent compounds.

16. A process as in claim 15 wherein the first fluorescent compound comprises fluorescein diacetate.

17. A process of claim 15 wherein the second fluorescent compound is unaffected by the microbiological or biochemical reaction provided by the source.

18. A process as in claim 15, wherein the detection comprises visual observation.

19. A process as in claim 15 wherein the source of the microbiological or biochemical reaction is selected from the group consisting of bacteria, plasmids, enzymes, yeasts, molds, animal cells and plant cells.

20. A process for detecting a change in the concentration of a microbiologically or biochemically active material produced by an enzyme-catalyzed reaction comprising:
(a) providing microdroplets containing:
(i) enzymes capable of producing the microbiologically or biochemically active material; and
(ii) at least two fluorescent compounds wherein at least one first fluorescent compound is capable of contributing to a change in the intensity or wavelength of a fluorescent emission from the first fluorescent compound in response to a change in the concentration of the microbiologically or biochemically active material, and at least one second fluorescent compound which is a reference standard, the proportion of which fluorescent compounds changes as the concentration of the microbiologically or biochemically active material changes, thereby producing a change in the intensity or wavelength of the fluorescent emissions from the fluorescent compounds;

(b) determining the intensity and wavelength of the fluorescent emissions from the fluorescent compounds;

(c) maintaining the microdroplets under conditions which allow the enzyme-catalyzed reaction to occur thereby causing a change in the amount of the microbiologically or biochemically active material; and (d) detecting the change in the concentration of the microbiologically or biochemically active material by determining the change in the intensity or wavelength of the fluorescent emission from the fluorescent compounds.

21. A process for detecting a change in the concentration of a microbiologically or biochemically active material comprising:

(a) providing microdroplets containing:
 (i) a source of the microbiologically or biochemically active material; and
 (ii) at least two fluorescent compounds wherein at least one first fluorescent compound is capable of contributing to a change in color by changing in fluorescent emission intensity in response to a change in concentration of the microbiologically or biochemically active material, and at least one second fluorescent compound which is a reference indicative of property of the microdroplets, the proportion of which fluorescent compounds changes as the concentration of the microbiologically or biochemically active material changes, thereby producing a color change in fluorescent emissions from the fluorescent compounds;

(b) determining the color of the fluorescent emission from the fluorescent compounds;

(c) maintaining the microdroplets under conditions which allow the concentration of the microbiologically or biochemically active material to change; and (d) detecting the property of the microdroplets and the change in the concentration of the microbiologically active material by determining the change in color of the fluorescent emission from the fluorescent compounds.

* * * * *

UNITED STATES PATENT AND TRADEMARK OFFICE
CERTIFICATE OF CORRECTION

PATENT NO. : 4,916,060
DATED : April 10, 1990
INVENTOR(S) : James C. Weaver

It is certified that error appears in the above-identified patent and that said Letters Patent is hereby corrected as shown below:

Column 10, Claim 1, line 56, change "for" to ---or---;

Column 11, Claim 3, line 17, change "Ophenylenediamine" to ---O-phenylenediamine---;

Column 11, Claim 8, line 47, change "fiber" to ---first---.

Signed and Sealed this

Second Day of April, 1991

Attest:

HARRY F. MANBECK, JR.

Attesting Officer

Commissioner of Patents and Trademarks